United States Patent
Dobrzyn et al.

(10) Patent No.: US 10,222,384 B2
(45) Date of Patent: Mar. 5, 2019

(54) METHOD FOR THE EARLY DIAGNOSIS OF A PRE-DIABETIC STATE AND TYPE 2 DIABETES

(71) Applicant: INSTYTUT BIOLOGII DOSWIADCZALNEJ IM. M. NENCKIEGO, POLSKIEJ AKADEMII NAUK, Warsaw (PL)

(72) Inventors: Agnieszka Dobrzyn, Warsaw (PL); Kamil Kozinski, Warsaw (PL); Pawel Dobrzyn, Warsaw (PL); Tomasz Bednarski, Warsaw (PL)

(73) Assignee: INSTYTUT BIOLOGII DOSWIADCZALNEJ IM. M. NENCKIEGO, POLSKIEJ AKADEMII NAUK, Warsaw (PL)

( * ) Notice: Subject to any disclaimer, the term of this patent is extended or adjusted under 35 U.S.C. 154(b) by 0 days.

(21) Appl. No.: 15/553,575

(22) PCT Filed: Feb. 26, 2016

(86) PCT No.: PCT/IB2016/051087
§ 371 (c)(1),
(2) Date: Aug. 24, 2017

(87) PCT Pub. No.: WO2016/135702
PCT Pub. Date: Sep. 1, 2016

(65) Prior Publication Data
US 2018/0017574 A1    Jan. 18, 2018

(30) Foreign Application Priority Data
Feb. 26, 2015   (PL) .......................................... 411390

(51) Int. Cl.
G01N 33/50    (2006.01)
G01N 33/68    (2006.01)
C12Q 1/686    (2018.01)
C12Q 1/6883   (2018.01)
G01N 33/538   (2006.01)

(52) U.S. Cl.
CPC ......... *G01N 33/6872* (2013.01); *C12Q 1/686* (2013.01); *C12Q 1/6883* (2013.01); *G01N 33/538* (2013.01); *G01N 33/6893* (2013.01); *C12Q 2600/158* (2013.01); *G01N 2333/46* (2013.01); *G01N 2333/4703* (2013.01); *G01N 2333/96425* (2013.01); *G01N 2800/042* (2013.01)

(58) Field of Classification Search
None
See application file for complete search history.

(56) References Cited

U.S. PATENT DOCUMENTS

2009/0220488 A1*   9/2009  Gardner ................. C07K 16/18
                                                   514/1.1

FOREIGN PATENT DOCUMENTS

| JP | 2010222330 A | 10/2010 |
|---|---|---|
| WO | 2008/109518 A1 | 9/2008 |
| WO | 2012/109538 A2 | 8/2012 |

OTHER PUBLICATIONS

Klingberg et al., Elevated Levels of WNT3A and Low Levels of Dickkopf-1 in Serum are Associated With Syndesmophyte Formation in Ankylosing Spondylitis, Ann Rheum Dis 2012, 71, Suppl 1, p. A64. (Year: 2012).*
Miyakoshi et al., Expression of Wnt4 in Human Pituitary Adenomas Regulates Activation of the B-Catenin-Independent Pathway, Endocr Pathol, 2008, 19, pp. 261-273. (Year: 2008).*
Li et al., Wnt4 is overexpressed in human pituitary adenomas and is associated with tumor invasion, Journal of Clinical Neuroscience, 21, 2014, pp. 137-141. (Year: 2014).*
Kawazoe et al., Significance of serum marker levels of Wnt/B-catenin signaling pathway in patients with systemic autoimmune disease under glucocorticoid therapy; a prospective study, Arthritis and Rheumatology, Oct. 2014, vol. 66, Sup. Suppl, 10, pp. 1-3, Abstract No. 233. (Year: 2014).*
Talaber et al., Wnt-4 Protects Thymic Epithelia Cells Against Dexamethasone-Induced Senescence, Rejuvenation Research, vol. 14, No. 3, 2011, pp. 241-248. (Year: 2011).*
Shen et al., Proteomic analysis of cerebrospinal fluid: toward the identification of biomarkers for gliomas, Neurosurg Refv, 2014, 37, pp. 367-380. (Year: 2014).*
Spillane et al., Upper-body resistance exercise augments vastus lateralis androgen receptor-DNA binding and canonical Wnt/B-catenin signaling compared to lower-body resistance exercise in resistance-trained men without an acute increase in serum testosterone, Steroids 98, Mar. 2015, pp. 63-71. (Year: 2015).*
Hu, F. B., "Inflammatory Markers and Risk of Developing Type 2 Diabetes in Women," Diabetes, American Diabetes Association, US, vol. 53, Mar. 1, 2004 pp. 693-700.
International Search Report, PCT/IB2016/051087, dated May 11, 2016.

* cited by examiner

*Primary Examiner* — Gary Counts
(74) *Attorney, Agent, or Firm* — Arrigo, Lee, Guttman & Mouta-Bellum LLP (57) ABSTRACT

We disclose a method of detecting the metabolic health of a mammal, including a human, by determining whether a given animal is normal, pre-diabetic or diabetic through the determination of the levels of Wnt4 and Wnt3a proteins in the blood serum.

4 Claims, 6 Drawing Sheets

METHOD FOR THE EARLY DIAGNOSIS OF A PRE-DIABETIC STATE AND TYPE 2 DIABETES

The present invention relates to the evaluation of the metabolic health of a mammal, including a human, by determining whether said animal is in a normal, pre-diabetic or diabetic state through the evaluation of the relative proportion of the level of the Wnt4 and Wnt3a proteins in blood plasma.

Type 2 diabetes (T2D) is one of the most common metabolic disorders, the prevalence of which is estimated to be about 171 million affected worldwide and this number is growing rapidly each year (Wild et al., 2004, Diabetes Care). This disease is characterized by a peripheral insulin resistance and pancreatic β-cell dysfunction (Kadowski, 2000, J Clin Invest). Obesity is the major predisposing factor for T2D. However, only a part of obese individuals will develop diabetes since they are not able to compensate for systemic insulin resistance by an adaptive increase in insulin secretion (Chan et al., 1994, Diabetes Care). The pancreatic β-cells ability to avoid hyperglycemia is a key factor in the prevention of T2D development. The compensatory response of β-cells is achieved mainly due to the expansion in β-cell mass (Kulkarni et al., 2004, J. Clin. Invest.). However, the exact mechanism that regulates β-cell plasticity remains far from clear. It has been demonstrated that β-cell mass in diabetic patients not only fails to expand, but it is also significantly reduced (Butler et al., 2003, Diabetes). Therefore, a treatment which could sustaine pancreatic β-cell adaptation process in diabetic patients would allow for the long-term restoration of normoglycemia.

There is a growing body of evidence that circulating factors can regulate β-cell function in a paracrine manner. Taking into account both, the proliferative properties of several adipocyte-released adipokines (Marques et al., 1998, Am J Phisiol.), and the key role of adipose tissue as an endocrine organ (Mc Gown et al., 2014, Clin Liver Dis.), it is justified to presume that this tissue might contribute to the β-cell mass adaptation. Fairy recently, human adipocytes were shown to secrete Wnt signaling molecules that were potent to induce β-cell proliferation and insulin secretion in vitro (Schinner et al., 2008, Diabetologia). Moreover, Wnt signaling plays an important role in muscle development (von Maltzahn et al., Trends in Cell Biol, 2012), heart hypertrophy (Bergmann, Circulation Research 2010) and in adipogenesis (Christodoulides et al., Trends Endocrinol Metab, 2009).

Genome-wide association studies have revealed several genomic loci that confer susceptibility for the development of T2D. At least 14 of those genes are implicated in islet growth and function. Additionally, seven of them are either components or targets of Wnt signaling pathway (Liu and Habener, Adv in Exp Med and Biol, 2010). Genetic variation within the gene encoding TCF7L2 has been shown as the most important T2D genetic risk factor in several human cohorts (Grant et al., 2006, Nat Genet). The TCF7L2-dependent Wnt pathway is involved in the pancreas development and function (Liu and Habener, 2010, dv Exp Med Biol; Logan and Nusse, 2004, Annu Rev Cel Dev Biol) as well as for cardiac hypertrophy (Malekar et al. Hypertention, 2010, Bergmann, Circulation Research 2010). Polymorphisms found in gene encoding Wnt pathway coreceptor—Lrp5—have been associated with the obesity phenotype (Twells et al., Genome Res, 2003) and missense mutation in Lrp6 have been linked to the risk of metabolic syndrome (Mani et al., Science, 2007).

Wnts, which are lipidated proteins, are capable of inducing pancreatic β-cell proliferation in vitro and in vivo (Rulifson et al., 2007, PNAS). Conditional knock-in of active form of β-catenin in mice successfully promotes the expansion of functional pancreatic β-cells (Heiser et al., Development, 2006), whereas a knock-in of a potent Wnt inhibitor, Axin, impaired proliferation of neonatal β-cells (Rulifson et al., 2007, PNAS). In addition, Wnt ligands stimulate insulin secretion in vitro (Schinner et al., 2008, Diabetologia). Reduction of TCF7L2 levels by siRNA treatement in both, isolated mouse and human islets, leads to a decreased glucose-stimulated insulin secretion (Shu et al., Diabetes, 2008; Loder et al., Biochem Soc Trans, 2008; da Silva et al., Diabetes, 2009). Moreover, the genetic ablation of the Wnt coreceptor encoding gene, Lrp5, impaired insulin secretion in mice, thus underlining the importance of Wnt signaling in pancreatic β-cell function (Fujino et al., 2003, PNAS).

On pathological stress, the heart reactivates several signaling pathways that traditionally were thought to be operational only in the developing heart. One of these pathways is the WNT signaling pathway. WNT controls heart development but is also modulated during adult heart remodeling. Activation of WNT signaling leads to progressive dilated cardiomyopathy (Malekar et al. Hypertention, 2010). Inhibition of nuclear β-catenin signaling downstream of the canonical WNT pathway significantly reduced postinfarct mortality and functional decline of LV function following chronic left anterior descending coronary artery ligation. WNT signaling also affects mobilization and horning of bone marrow-derived vasculogenic progenitor cells. Finally, heart-specific WNT/β-catenin interaction partners have been identified that will possibly allow targeting this pathway in a tissue-specific manner. However, no study linking WNT signaling and diabetic cardiomyopathy has been published to date.

Growing data about circulating factors that can regulate β-cell and cardiomyocyte function in paracrine manner bring new way of thinking about cross-talk between different type of tissue in case of pathophysiology of type 2 diabetes. For instance, liver via betatrophin can specifically promotes pancreatic β-cell proliferation and expands β-cell mass (Yi et al., 2013, Cell). Moreover, Palau and colleges showed that obesity induces downregulation of IGFBP3 secretion from adipose tissue depot surrounding the pancreas thus leading to stimulation of β-cell proliferation rate (Palau et al., 2012, Endocrinology).

The present invention relates to method of detecting a pre-diabetic state or diabetes, particularly type II diabetes, characterized in that it comprises assessing the level of a protein selected from Wnt4 and Wnt3a in a biological sample from an individual, particularly in the serum, wherein an abnormal level of the protein is indicative of a prediabetic state or type II diabetes, wherein preferably:

A pre-diabetic state is indicated by a reduced level of Wnt4 or an elevated level of Wnt3a, or by the occurrence of these abnormalities at the same time, Diabetes, especially Type II diabetes, is indicated by an increased Wnt4 level and a decreased level of Wnt3a.

Preferably, the protein level is examined using a known technique, such as ELISA or an immunoassay, in particular a strip test.

Preferably, the subject exhibits concomitant clinical symptoms or bears a genetically determined predisposition to diabetes, particularly type II diabetes.

Another subject of the invention is the use of the levels of a protein selected from Wnt4 and Wnt3a, especially in the serum, for identifying a pre-diabetic state or diabetes.

Unexpectedly, according to the present invention, our data indicate the existence of a cross-talk between insulin resistant tissues s.e. adipose or muscle and pancreatic β-cells. This phenomenon occurs in order to adapt to the rising demands of insulin linked to the onset of diabetes. According to this, we observed that insulin resistant adipocytes secrete factors that are able to induce insulin secretion and pancreatic β-cells proliferation. This is suggested by finding that INS1-E cells incubated in fat cell conditioned medium (FCCM) from insulin resistant adipocytes incorporate excessive amount of BrdU and secrete more insulin in comparison to cells incubated in FCCM from insulin sensitive adiocytes. In line with these studies, FCCM treated cells exhibited upregulation of Wnt target genes such as cycD1 and c-myc which are involved in proliferative effect (Rulifson et al., 2007, PNAS). We also found increased expression of Anp and Bnp genes, markers of cardiac hypertrophy, in cardiomyocyes treated with FCCM from insulin resistant adipocytes indicating that insulin resistant adipocytes secret factors contributing to cardiomyocyte hypertrophy, the first feature of diabetic cardiomyopathy. Furthermore, we have proved that these phenomena are mediated through Wnt signaling since usage of sFRP—potent extracellular Wnt inhibitor—abolished induction of insulin secretion and proliferation as well as cardiac hypertrophy caused by adipose-derived factors. Therefore, we have focused upon the search for adipokines that could be responsible for β-cell adaptation process and heart dysfunction, on Wnt ligands and inhibitors. In our in vitro studies, on insulin sensitive cells such as C2C12 myotubes and 3T3-L1 adipocytes, we have found that Wnt4—inhibitor of canonical Wnt pathway was downregulated, and Wnt3a—canonical Wnt activator-was upregulated in case of insulin resistant adipocytes and myotubes. We also found that insulin resistant cells (both C2C12 myotubes and 3T3 adipocytes) secrete more Wnt3a and less Wnt4 compared to insulin sensitive cells.

Figure 9:
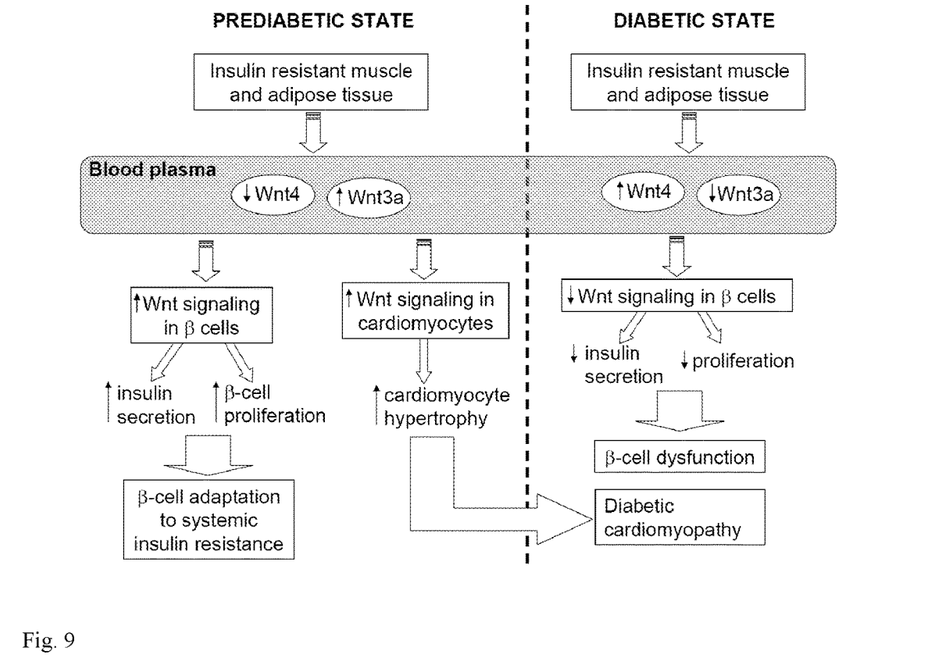

These two Wnt ligands were studied more extensively in diet-induced diabetic in vivo model. We established 8-weeks HF-fed rats as pre-diabetic model since their β-cells properly adapted to systemic insulin resistance. Our studies demonstrated that in pre-diabetic state downregulation in Wnt4 and upregulation in Wnt3a expression in insulin resistant muscle and adipose tissue (and parallel changes in the level of Wnt4 and Wnt3a secession into blood plasma from these tissues) are responsible for activation of Wnt signaling pathway in pancreatic β-cells in a endocrine manner. Accumulation of active β-catenin, main element of Wnt signaling pathway and indicator of Wnt activation, correlates with increase in insulin secretion and β-cell proliferation of isolated pancreatic islets (FIG. 9). On the other hand, prolongation of HF-diet until 16-weeks period is responsible for a severe diabetic onset since their β-cells no longer adapt to systemic insulin resistance. Interestingly, in this state we have found that expression profile of Wnt4 and Wnt3a is opposite to pre-diabetic state in favor of downregulation of canonical Wnt signaling. Lack of Wnt activation in pancreatic islets isolated from diabetic rats was correlated with downregulation of β-cell proliferation rate and deficiency in insulin production (FIG. 9). Obtained results demonstrate that alterations in secretion profile of canonical activator (Wnt3a) and inhibitor (Wnt4) from insulin resistant tissues during T2D development are responsible for triggering progression from pre-diabetic to diabetic state.

Furthermore, activation of Wnt signaling in cardiomyocytes in pre-diabetic state leads to cardiac hypertrophy, one of the key features of diabetic cardiomyopathy. Early diagnosis of pre-diabetic state is therefore imperative to prevent both T2D progression and diabetes associated cardiac dysfunction.

Figure 10:
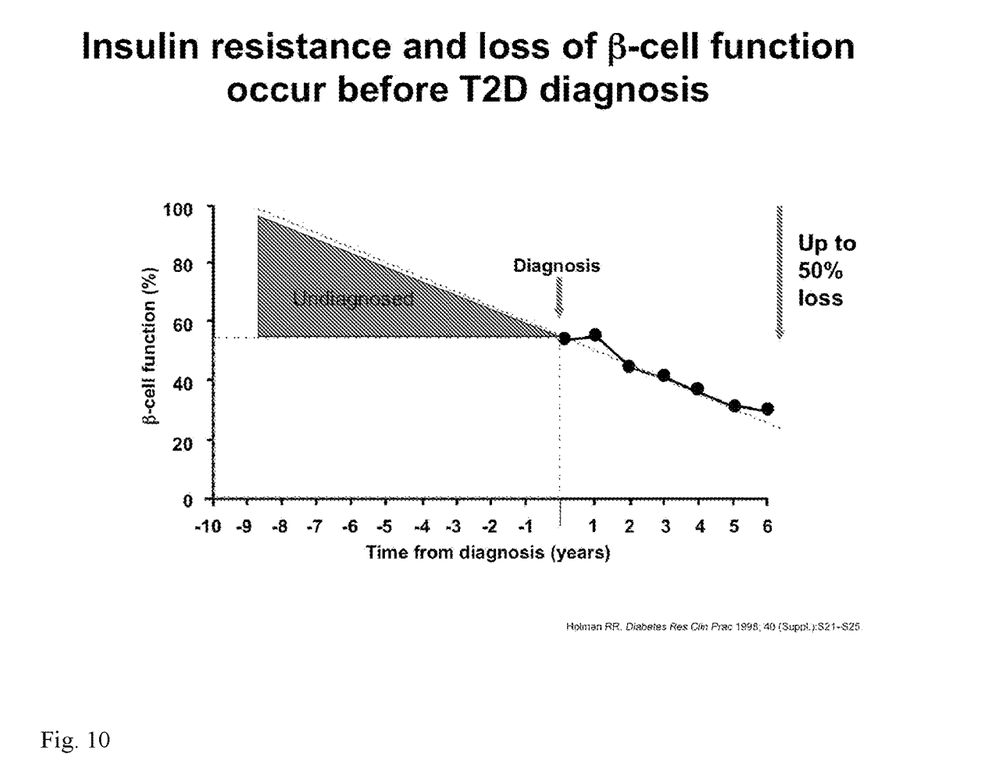
FIG. 10 shows the extrapolation of the observed rate of decline of β-cell function in diet-treated subjects suggests that loss of β-cell function can begin at least 10 years before type 2 diabetes (T2D) diagnosis.

As can be seen from the FIG. 10, T2D develops over a 10 year period before its actual clinical onset. The insulin resistance diagnosis is usually late, and usually occurs nearly 10 years after the onset of changes, usually too late to treat. The currently existing tests used for diagnosis of insulin resistance/pre-diabetic state include hyperinsulinemic-euglycemic clamp (that is expensive and requires special equipment available only in specialized clinics) and plasma insulin measurement (more available but expensive and therefore not performed during a routine medical tests). Thus far, no test exists which would be capable of predicting the onset of T2D before its development, in an easy and inexpensive way, particularly earlier and more easily than the increased insulin secretion noted in pre-diabetic states.

The goal of the present invention is to deliver such an easily performed test facilitating the diagnosis particularly of early pre-diabetic states which precede the full form of diabetes.

Such a Stated Problem has been Unexpectedly Solved by the Present Invention.

BRIEF DESCRIPTION OF THE INVENTION

The invention is summarised in FIG. 9. Briefly, in pre-diabetic state insulin resistant tissues (skeletal muscle and adipose tissue) produce and secrete into the blood plasma less inhibitor (Wnt4) and more activator (Wnt3a) of canonical Wnt signaling pathway what leads to upregulation of Wnt signaling in pancreatic β-cells and cardiomyocytes through an endocrine manner. Activated Wnt pathway triggers adaptation of β-cells to the systemic insulin resistance by increasing insulin secretion and β-cells proliferation rate. Simultaneously, increased Wnt signalling in cardiomyocytes leads to upregulation of hypertrophic genes, ANP and BNP, and initiate cardiomyocyte hypertrophy, a known hallmark of diabetic cardiomyopathy. In diabetic state insulin resistant tissues produce and secrete into blood plasma more inhibitor (Wnt4) and less activator (Wnt3a) of canonical Wnt signaling pathway what has impact on downregulation of Wnt signalling in pancreatic β-cells. Reduction of Wnt pathway activation negatively affect β-cell adaptation to the systemic insulin resistance and leads to pancreatic islet dysfunction. Thus, the relative proportion of the level of the Wnt4 and Wnt3a proteins in blood plasma might be used as biomarker of pre-diabetic and diabetic states. The present invention also relates to the use of Wnt4 and Wnt3a as therapeutic targets for alleviating the effects of diabetic beta cell insufficiency, as well as cardiac myopathy.

FIGURES

The following Figures are provided to better illustrate the nature of the present invention, wherein:

FIG. 1 shows that fat cell conditioned medium (FCCM) from insulin resistant adipocytes (16:0) stimulates proliferation, insulin secretion and Wnt signaling in INS-1E cells. A. 16:0 incubation leads to insulin resistance in 3T3-L1 adipocytes. Western blotting was performed on extracts from BSA- and 16:0-incubated 3T3-L1 adipocytes with antibodies against phosphorylated (Ser473) and total AKT kinase. B. Activation of Wnt reporter vector (TOP) in INS-1E cells under FCCM treatment. INS-1E cells were transfected with TOP reporter vector bearing luciferase reporter gene under control of TCF-binding sites or FOP reporter vector with mutated TCF-binding sites. The luciferase activity is expressed as relative light units (RLU) measured as quotient of TOP and FOP values. C. Induction of INS-1E proliferation under FCCM treatment. Proliferation rate is normalized to cells treated with control (DMEM) medium. D. Stimulation of INS-1E insulin secretion under FCCM treatment in low glucose (2.5 mM) and high glucose (15 mM) conditions. n=3; mean±SD*p<0.05 vs DMEM, #p<0.05 vs FCCM (BSA) control.

FIG. 2 shows that fat cell conditioned medium (FCCM) from insulin resistant adipocytes (16:0) contains Wnt ligands which induce INS-1E proliferation and insulin secretion through Wnt signaling pathway. A. Fat cell conditioned medium from insulin resistant adipocytes (FCCM 16:0) activates Wnt reporter vector (TOP) in INS-1E cells. This effect is abolished by sFRP, a potent extracellular Wnt inhibitor, treatment. INS-1E cells were transfected with TOP reporter vector bearing luciferase reporter gene under control of TCF-binding sites or FOP reporter vector with mutated TCF-binding sites. The luciferase activity is expressed as relative light units (RLU) measured as quotient of TOP and FOP values. B. Fat cell conditioned medium from insulin resistant adipocytes (FCCM 16:0) induces expression of Wnt signaling-related genes in INS-1E cells. This effect is abolished by sFRP treatment, β-actin was used as a normalization control. C. Stimulation of INS-1E insulin secretion under FCCM treatment in low glucose (2.5 mM) and high glucose (15 mM) conditions is abolished by sFRP treatment. D. Induction of INS-1E proliferation under FCCM (16:0) treatment is abolished by sFRP treatment. Proliferation rate of INS-1E cells is expressed as relative to cells treated with control (DMEM) medium; n=3; mean±SD*p<0.05 vs DMEM, #p<0.05 vs FCCM (BSA), &p<0.05 vs FCCM (16:0).

FIG. 4 shows the gene expression profile, cellular protein levels and secretion of Wnt4 and Wnt3a are changed in insulin resistant adipocytes and myotubes. A. Real Time PCR analysis of Wnt-related genes in 3T3-L1 adipocytes (A1) and C2C12 myotubes (A2). β-actin was used as a normalization control. n=3; mean±SD*p<0.05 vs 3T3 (BSA). B. In insulin resistant (16:0) adipocytes (B1) and myotubes (B2) content of Wnt4 protein is reduced and content of Wnt3a protein is increased in comparison to control insulin sensitive (BSA) cells. Western blotting was performed on 3T3-L1 and C2C12 cell lysates using antibody against Wnt4 and Wnt3a proteins. β-tubulin was used as a loading control. C. Secretion level of Wnt4 and Wnt3a from 3T3 adipocytes and C2C12 myotubes. Conditioned medium from insulin resistant (FCCM 16:0) adipocytes (C1) and myotubes (MCCM 16:0) (C2) contain less Wnt4 and more Wnt3a in comparison to media from control insulin sensitive (BSA) cells. Western blotting was performed on FCCM and MCCM using antibody against Wnt4 and Wnt3a proteins. Ponceau staining was used as a loading control.

FIG. 5 shows the gene expression, protein level and secretion rate of Wnt4 and Wnt3a in insulin resistant white adipose tissue and gastrocnemius muscle are changed in prediabetic state. A. Glucose tolerance test was performed on 8 weeks CHOW- and pre-diabetic HF-fed rats after overnight fasting. n=6; mean±SD*P<0.05 vs. CHOW. B. In insulin resistant adipose tissue from pre-diabetic rats gene expression (B1) and protein level (B2) of Wnt4 are reduced and Wnt3a are increased in comparison to tissues from CHOW fed rats. β-actin was used as a normalization control. n=6; mean±SD*p<0.05 vs CHOW. C. In insulin resistant skeletal muscle from pre-diabetic rats gene expression (C1) and protein level (C2) of Wnt4 and Wnt3a are significantly changed. D. The content of Wnt4 and Wnt3a in blood plasma of pre-diabetic rats. Western blotting was performed on a blood serum from CHOW and HF fed rats using antibody against Wnt4 and Wnt3a proteins. Ponceau staining was used as a loading control. n=6

FIG. 6 shows the gene expression, protein level and secretion rate of Wnt4 and Wnt3a in insulin resistant white adipose tissue and gastrocnemius muscle in diabetic state. A. Glucose tolerance test was performed on 16 weeks CHOW- and diabetic HF-fed rats after overnight fasting. n=6; mean±SD*P<0.05 vs. CHOW. B. Gene expression (B1) and protein level (B2) of Wnt4 are reduced and Wnt3a rats are increased nn insulin resistant adipose tissue from diabetic (HF) rats in comparison to tissues from healthy (CHOW fed) rats. β-actin was used as a normalization control. n=6; mean±SD*p<0.05 vs CHOW. C. In insulin resistant skeletal muscle from diabetic (HF) rats gene expression (C1) and protein level (C2) of Wnt4 and Wnt3a are significantly changed. D. The content of Wnt4 and Wnt3a in blood plasma of diabetic (HF) rats. Western blotting was performed on a blood serum from CHOW and HF fed rats using antibody against Wnt4 and Wnt3a proteins. Ponceau staining was used as a loading control. n=6

FIG. 9 shows that Wnt ligands contribute to β-cell adaptation towards systemic insulin resistance. In prediabetic state insulin resistant tissues (adipose tissue and skeletal muscle) produce less inhibitor (Wnt4) and more activator (Wnt3a) of canonical Wnt signaling pathway what leads to upregulation of Wnt signaling in pancreatic β-cells through an endocrine manner. Activated Wnt pathway triggers adaptation of β-cells to the systemic insulin resistance by increasing insulin secretion and β-cell proliferation rate. Simultaneously, increased Wnt signalling in cardiomyocytes leads to upregulation of hypertrophic genes, ANP and BNP, and initiate cardiomyocyte hypertrophy, a known hallmark of diabetic cardiomyopathy. In diabetic state insulin resistant tissues produce more inhibitor (Wnt4) and less activator (Wnt3a) of canonical Wnt signaling pathway what has impact on downregulation of Wnt signalling in pancreatic β-cells. Reduction of Wnt pathway activation negatively affect β-cell adaptation to the systemic insulin resistance and leads to pancreatic islet dysfunction.

The invention is also demonstrated by the following non-limiting examples, but the person skilled in the art will immediately see additional developments, which nevertheless do not fall outside of the scope of the present invention.

EXAMPLE 1

Cell Conditioned Media from Insulin Resistant Adipocytes (FCCM) and from Insulin Resistant Myotubes (MCCM) Contain Factors which Induce Wnt Signaling, Proliferation and Insulin Secretion in INS-1E β-Cells Through Wnt Signaling Pathway.

Figure 1:
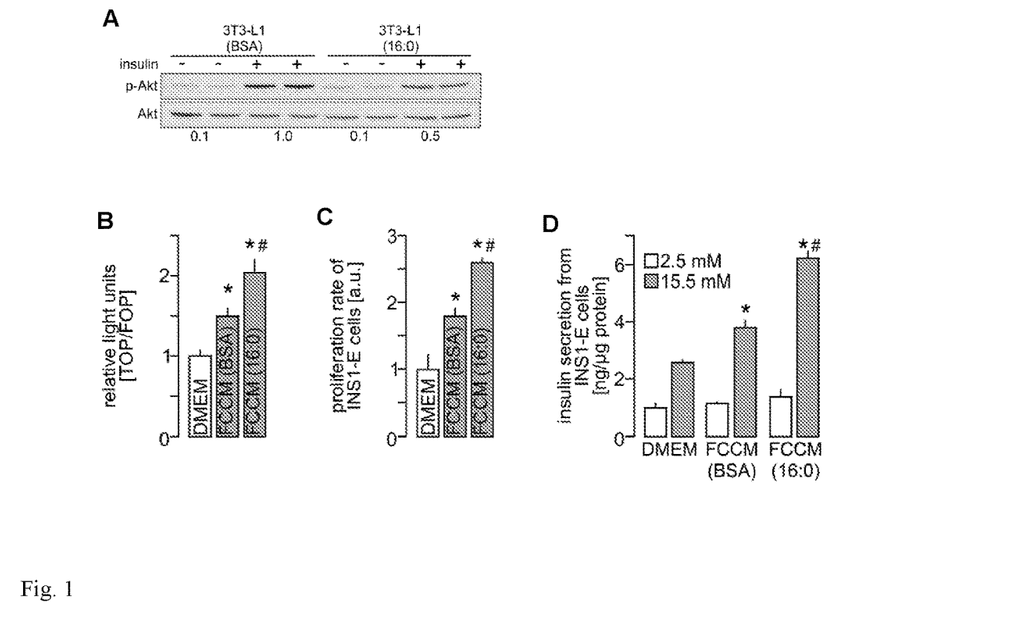

In order to investigate functional interaction between insulin resistant tissues and β-cells in context of β-cell adaptation to systemic insulin resistance, we used fat cell conditioned medium (FCCM) from insulin resistant adipocytes and a medium from insulin resistant C2C12 myotubes (MCCM) to treat INS-1E cells. Insulin resistance was induced by palmitate (16:0) treatment (FIG. 1A). FCCM from human healthy adipocytes (BSA) induced proliferation, insulin secretion and Wnt signaling in β-cells (FIG. 1B-D). Interestingly, we have found that conditioned medium from insulin resistant adipocytes increased Wnt signaling, proliferation and insulin secretion in β-cells to a higher level than treatment with medium from insulin sensitive cells (FIG. 1B-D).

To verify the influence of adipose-derived factors on Wnt signaling activity in β-cells we have used luciferase reporter assay. Induction of TCF reporter vector in INS-1E cells treated with FCCM (16:0) for 24 h was increased approximately twice in comparison to control cells, while FCCM (BSA) drived 1.5 times higher induction of TCF transcriptional activity (FIG. 1 A). We assessed the effect of FCCM on INS-1E proliferation rate by BRDu incorporation test. FCCM (16:0) treatment increased INS-1E proliferation by 2.6 times over the control cells whereas FCCM (BSA) caused only 1.8 times higher induction of proliferation rate (FIG. 1B). Similarly, when INS-1E cells were stimulated with medium from insulin resistant adipocytes, insulin secretion was increased 2.4 times at high glucose (15.5 mM) conditions whereas FCCM (BSA) caused less than 1.5 fold induction in comparison to control cells (FIG. 1C). These results clearly demonstrate that adipose-derived factors from insulin resistant adipocytes are involved in the induction of insulin secretion, proliferation and Wnt signaling pathway in β-cells.

Figure 2:
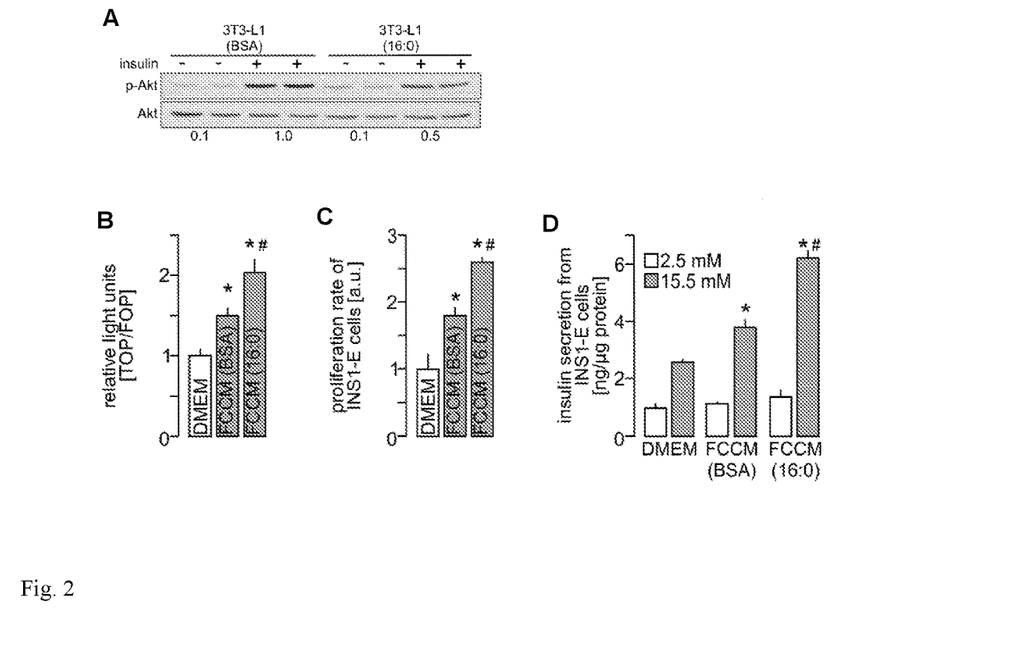
Figure 3:
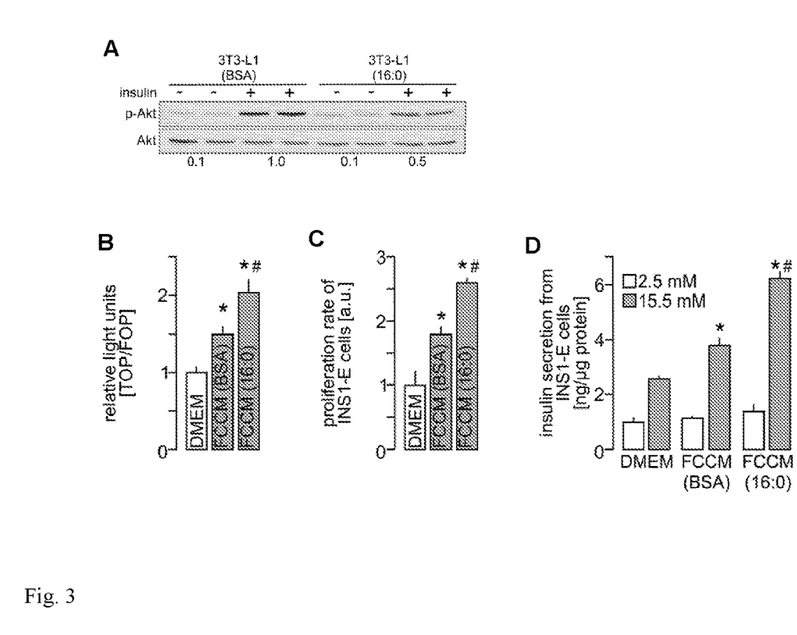
FIG. 3 shows that fat cell conditioned medium (FCCM) from insulin resistant adipocytes (16:0) contains Wnt ligands which induce pancreatic islets proliferation and insulin secretion through Wnt signaling pathway. A. Fat cell conditioned medium from insulin resistant adipocytes (FCCM 16:0) induces expression of Wnt signaling related genes in pancreatic islets. β-actin was used as a normalization control. B. FCCM stimulates insulin secretion in pancreatic islets in low glucose (2.75 mM) and high glucose (16.5 mM) conditions and (C.) increases proliferation rate of □-cells in pancreatic islets. These effects are abolished by sFRP treatment. n=3; mean±SD*p<0.05 vs DMEM, #p<0.05 vs FCCM (BSA), &p<0.05 vs FCCM (16:0). sFRP—a potent extracellular Wnt inhibitor

Recently Wnt activators were described as novel adipokines (Shinner et al. 2007; Shinner at al., 2008). To test whether Wnt activation in β-cells under FCCM (16:0) treatment is triggered specifically by adipose-derived Wnt activators but not by other adipokines, we have used soluble Wnt antagonist (sFRP) to treat, either INS-1E β-cells or isolated pancreatic islets, together with fat cell conditioned medium. The Wnt3a conditioned medium from L-Wnt3a cells was applied as a positive control. The content of active (unphosphorylated) beta-catenin, the key element of canonical Wnt signaling pathway, was then analysed by immunoblotting in both, INS-1E and pancreatic islets. Interestingly, the highest accumulation of beta-catenin was observed in INS-1E cells and islets incubated in medium from insulin resistant adipocytes, and it was significantly increased in comparison to controls. More importantly, this effect was completely abolished when sFRP was applied. In order to verify whether Wnt signaling affects proper functioning of β-cells, sFRP was again administrated into the experimental design. The induction effect of medium from insulin resistant adipocytes on secretory capacity of INS1-E cells and pancreatic islets was inhibited by sFRP at both, low- and high-glucose conditions (FIG. 2 C and FIG. 3 B). Similarly, FCCM from insulin resistant adipocytes stimulated proliferation of INS-1E and pancreatic islets and this effect was reduced after sFRP (FIG. 2 D. and FIG. 3 C.). The obtained data suggest that FCCM (16:0) medium contains Wnt ligands potent to stimulate proliferation and induce insulin secretion of β-cells.

We have also determined expression levels of Wnt-related genes—CTNNB1 which encodes beta-catenin, and two Wnt target genes: cmyc and cyclinD1. Expression of the aforementioned genes was upregulated in case of FCCM (16:0) treatment (~7.0, ~1.9 and ~24.0 fold change, respectively) and showed higher induction level than FCCM (BSA) treated INS-1E cells (~2.0, ~1.0, ~18.0) (FIG. 2 A). Similar outcome was demonstrated in isolated pancreatic islets (FIG. 3 A). The effect of increased Wnt-related genes expression was diminished bys FRP. Additionally, activation of Wnt in INS-1E cells under FCCM (16:0) treatment was confirmed by Wnt reporter assay and showed 30% higher induction level in comparison to FCCM (BSA) treated INS-1E cells. The activation effect was abolished by addition of sFRP to the fat cell conditioned medium. Above results indicate that fat cell conditioned medium from insulin resistant adipocytes contains Wnt signaling activators which are sufficient to induce Wnt pathway in β-cells.

EXAMPLE 2

Expression Profile of Genes Encoding Wnt Ligands, Protein Level of Wnt4 and Wnt3a and Rate of Secretion of these Proteins are Changed in Insulin Resistant Adipocytes and Myotubes.

Figure 4:
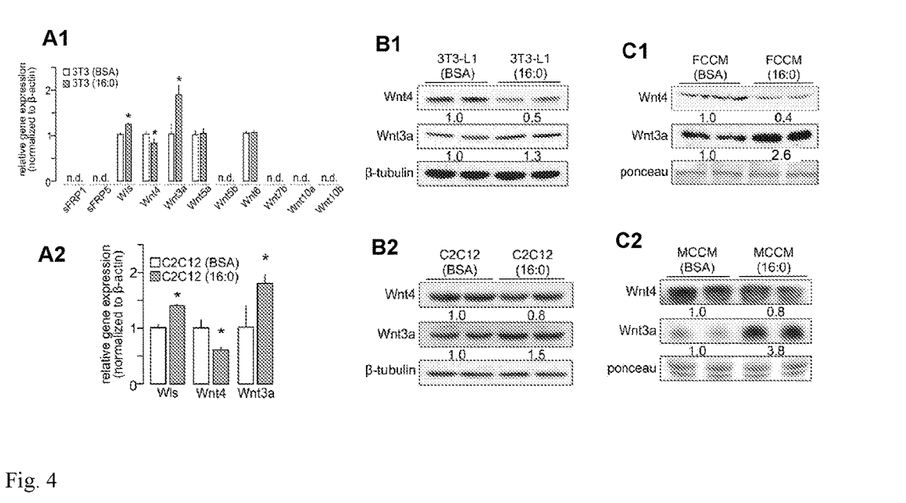

Since we have shown that adipocytes produce Wnt activators sufficient to activate Wnt signaling in β-cells and to trigger insulin secretion and proliferation, we wanted to examine the identity of the Wnt ligands responsible for such stimulatory effect. We have performed Real-Time PCR screening in insulin resistant adipocytes in order to look for the possible changes in expression of the genes encoding Wnt ligands. Insulin resistance in 3T3-L1 adipocytes was induced by 16:0 treatment and confirmed by a decrease of AKT kinase phosphorylation state under insulin stimulation—the main downstream element of insulin pathway (FIG. 1 A). We have verified a wide reperoitre of Wnt related genes but only three of them exhibited changes in gene expression after insulin resistance induction in 3T3-L1 adipocytes (FIG. 4 A). Interestingly, expression of wls, which encodes wntless protein exclusively involved in secretion of Wnt ligands, was upregulated by ~1.2 fold change in insulin resistant adipocytes. Moreover expression of gene encoding Wnt4 in insulin resistant 3T3-L1 cells was downregulated by ~0.8 fold change in comparison to insulin sensitive cells. Wnt4 is known inhibitor of canonical Wnt signaling pathway (Bernard et al., 2008). Additionally, gene encoding canonical Wnt activator—Wnt3a—was overexpressed by ~1.8 fold change in insulin resistant adipocytes (4 A1). In insulin resistant C2C12 myotubes (16:0) expression of Wnt4 was reduced by 40% and expression of Wnt3a 1.8 times higher compared to healthy (BSA) cells (FIG. 4 A2). Furthermore, these results were paralleled by changes in the level of these proteins in cell lysates (FIG. 4 B1-B2). Importantly, changes in gene expression and intracellular protein levels of Wnt4 and Wnt3a were accompanied by changes in the rate of secretion of these proteins from insulin resistant 3T3 adipocytes and C2C12 myotubes. The content of Wnt4 in cell conditioned medium from insulin resistant 3T3-L1 adipocytes (FCCM 16:0) and in cell conditioned medium from insulin resistant C2C12 myotubes (MCCM 16:0) where reduced by 0.5 and 0.8 fold, respectively (FIG. 4 C1-C2) but Wnt3a expression was increased by 2.6 and 3.8 fold change, respectively (FIG. 4C1-C2).

EXAMPLE 3

Expression Profile of Wnt4 and Wnt3a in Insulin Resistant Tissues and the Secretion Rate of these Proteins into Blood Plasma is Changing During Progression of Diabetes.

Figure 5:
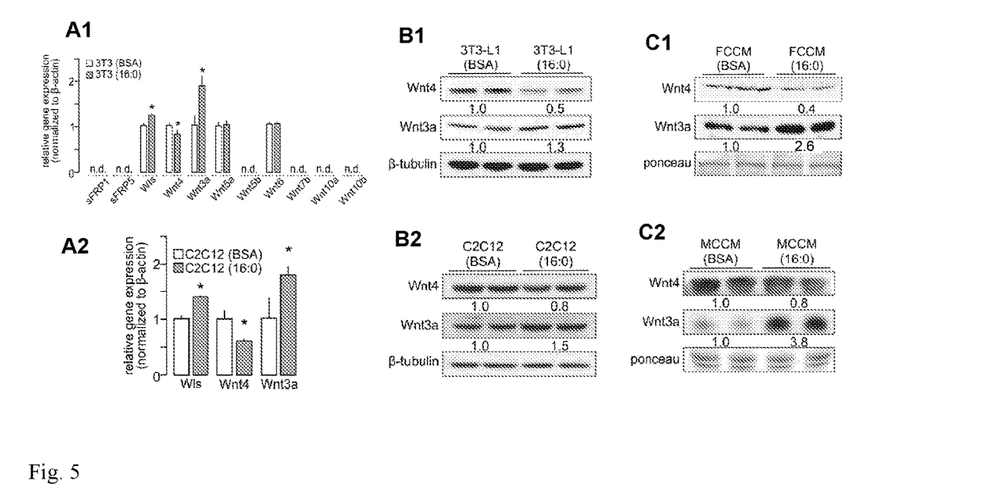
Figure 6:
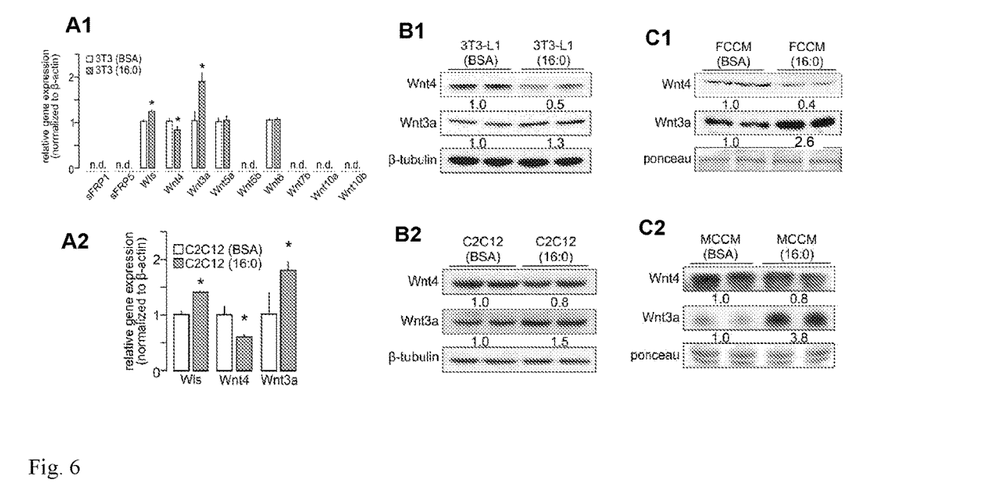

To investigate whether data from in vitro studies are consistent with in vivo changes, we analyzed expression of Wnt4 and Wnt3a in white adipose tissue and gastrocnemius muscle in prediabetic and diabetic animal models. Wistar rats were fed with high fat (HF) diet for 8 weeks or 16 weeks to induce insulin resistance of peripheral tissues and diabetes, respectively, as showed by glucose tolerance test (FIG. 5A, 6A). Both HF-fed groups of animals showed impaired glucose metabolism in comparison to CHOW-fed groups. Next, we analyzed expression profile and protein content of Wnt4 and Wnt3a in visceral adipose tissue and gastrocnemius muscle. In pre-diabetic state, expression of Wnt4 was downregulated (~0.4 fold change) while expression of Wnt3a was upregulated (~1.6 fold change) in insulin resistant adipose tissue in comparison to adipose tissue from healthy CHOW-fed rats (FIG. 5 B1). Similar results were also obtained at the protein levels of Wnt4 and Wnt3a in adipose tissue (~0.6 and ~1.8 fold change respectively) (FIG. 5 B2). The expression profile of Wnt4 and Wnt3a were significantly changed in insulin resistant gastrocnemius muscle compared with controls (FIG. 5C1-C2). Furthermore, the secretion rate of these proteins from insulin resistant tissues was significantly affected and, as a consequence, Wnt4 protein level in blood plasma was decreased (by 20%) while Wnt3a protein level was significantly increased (~11.7 fold change) in prediabetic rats compared to healthy animals (FIG. 5D).

Interestingly, in diabetic rats (16 weeks of HF diet), the expression of Wnt4 was significantly increased and Wnt3a was significantly reduced in both white adipose tissue (FIG. 6B1) and skeletal muscle (FIG. 6 C1) in comparison to healthy animals. Additionally, protein level of Wnt4 was increased by 30% in adipose tissue (FIG. 6 B2) and by 60% in skeletal muscle (FIG. 2 B2) and protein level of Wnt3a was not changed in adipose tissue and reduced by 60% in skeletal muscle (FIG. 6 B2, C2). More importantly, Wnt4 protein level in blood plasma was 2.1 times increased and Wnt3a was 20% depressed in diabetic rats compared to healthy animals (FIG. 6D).

EXAMPLE 4

Figure 7:
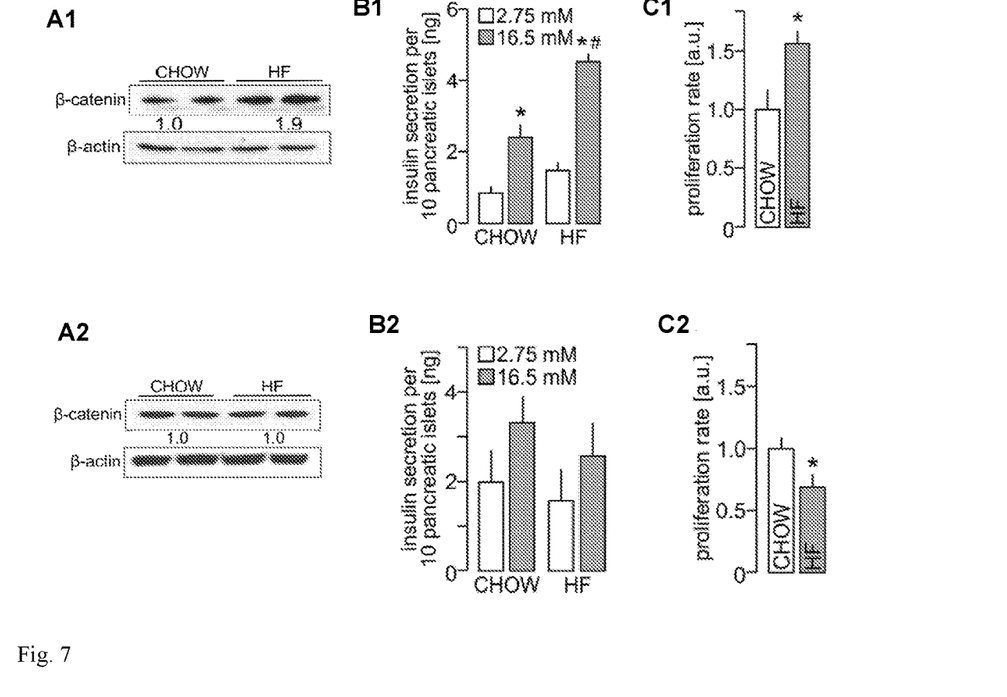
FIG. 7 shows the state of β-cell adaptation towards systemic insulin resistance in HF fed rats. A. Active β-catenin content in pancreatic islets from pre-diabetic ($A_1$) and diabetic ($A_2$) HF fed rats. Western blotting was performed on pancreatic islets extracts using antibody against active β-catenin. β-actin was used as a loading control. B. Insulin secretion of pancreatic islets from pre-diabetic ($B_1$) and diabetic ($B_2$) HF fed rats in low glucose (2.75 mM) and high glucose (16.5 mM) conditions. n=6; mean±SD*p<0.05 vs CHOW C. Proliferation rate of □-cells in pancreatic islets from pre-diabetic ($C_1$) and diabetic ($C_2$) HF fed rats. Proliferation rate of pancreatic islets is expressed as quotient of BrdU dots and area of pancreatic islet section. n=15; mean±SEM FIG. 8. shows that fat cell conditioned medium (FCCM) from insulin resistant adipocytes (16:0) contains Wnt ligands which induce cardiomyocyte hypertrophy through Wnt signaling pathway. A. Protein level of ANP in HL1 (A1) and H9C2 (A2) cardiomyocytes. B.-C. Gene expression of ANP and BNP in HL1 (B1-C1) and H9C2 (B2-C2) cardiomyocytes. n=3; mean±SD*p<0.05 vs Claycomb, #p<0.05 vs FCCM (BSA), &p<0.05 vs FCCM (16:0). sFRP—a potent extracellular Wnt inhibitor, ANP, BNP—markers of cardiac hypertrophy

Activation of Wnt Signaling is Correlated with β-Cell Adaptation to Systemic Insulin Resistance The next step in our studies was to investigate how changes in expression profile of Wnt ligands in insulin resistant tissues influence functioning of the pancreatic β-cells within our pre-dabetic and diabetic animal models. Western blot analysis of pancreatic islets isolated from pre-diabetic rats showed accumulation of active beta-catenin (1.9 fold change) (FIG. 7 A1). This phenomenon was associated with increased insulin secretion (~1.8 fold change) (FIG. 7 B1) and proliferation rate (~1.6 fold change) (FIG. 7C1). In contrast, there was no difference in the level of active beta-catenin between pancreatic islets isolated from diabetic rats compared to healthy animals (FIG. 7 A2). Additionally, in case of islets originating from diabetic animals, insulin secretory capacity was no longer affected (FIG. 7 B2) and their proliferation rate was decreased by 0.4 fold change in comparison to pancreatic islets isolated from CHOW-fed rats (FIG. 7 C2).

EXAMPLE 5

Cell Conditioned Media from Insulin Resistant Adipocytes (FCCM) Contain Factors which Induce Wnt Signaling and Cardiomyocyte Hypertrophy Through Wnt Signaling Pathway.

Figure 8:
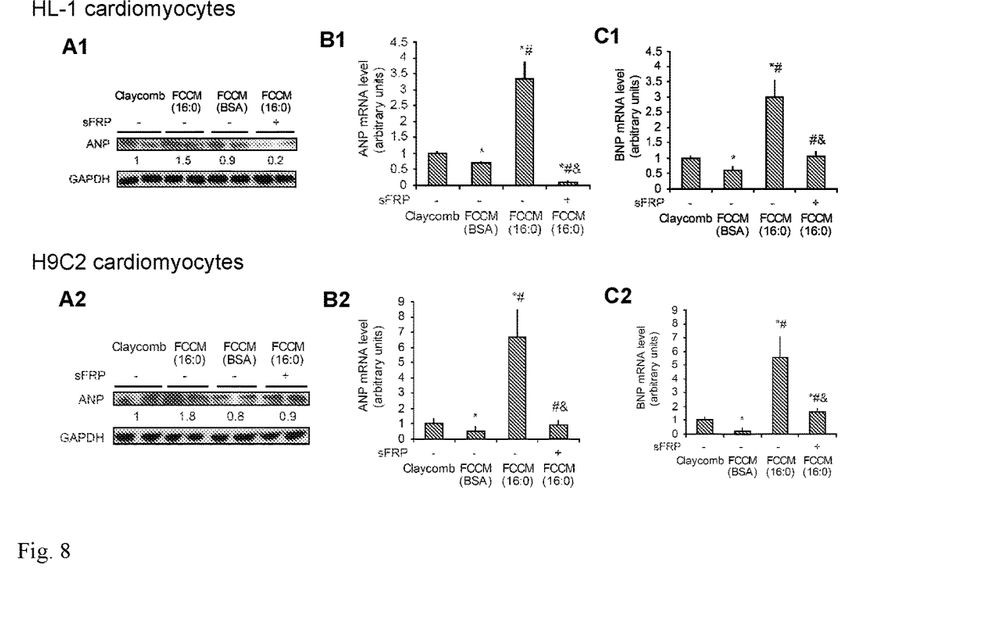

Activation of Wnt signaling in the heart might lead to maladaptive cardiac hypertrophy (Malekar et al., Hypertantion 2010). We tested the hypothesis that Wnt ligands secreted by insulin resistant tissues activate Wnt signaling in cardiomyocytes and thereby induce cardiomyocyte hypertrophy—one of the hallmarks of diabetic cardiomyopathy. Experiments were performed on two different cardiomyocyte cell lines, HL1 and H9C2. We analyzed the expression of atrial natriuretic peptide (ANP) and brain natriuretic peptide (BNP), two key markers of cardiac hypertrophy. Incubation of with FCCM from insulin resistant adipocytes (16:0) led to increase in ANP protein level by 50% and 80% in HL1 and H9C2 cardiomyocytes, respectively, compared to FCCM (BSA) controls (FIG. 8A1-A2). Also, gene expression of ANP (FIG. 8 B1-B2) as well as gene expression of BNP (FIG. 8C1-C2) were significantly induced by FCCM from insulin resistant adipocytes in the both tested cardiomyocyte lines, compared to controls. Upregulation of ANP and BNP markers by FCCM from insulin resistant adipocytes in cardiomyocytes was abolished after sFRP (a potent extracellular Wnt inhibitor) treatment (FIG. 8). The obtained data suggest that Wnt ligans secreated by insulin resistant tissues are potent to activate Wnt signaling in the heart and to stimulate catrdiomyocyte hypertrophy, and might be one of the key factors leading to progression of diabetic cardiomyopathy (FIG. 9).

The invention claimed is:
1. A method comprising:
providing a blood serum sample from a patient;
measuring the level of Wnt4 protein in the blood serum sample; and
measuring the level of Wnt3a protein in the blood serum sample and detecting an increased level of Wnt3a.

2. The method of claim 1, further comprising detecting a decreased level of Wnt4.

3. A method comprising:
   providing a blood serum sample from a patient;
   measuring the level of Wnt4 protein in the blood serum sample; and
   measuring the level of Wnt3a protein in the blood serum sample and detecting an increased level of Wnt4.

4. The method of claim 3, further comprising detecting a decreased level of Wnt3a.

* * * * *